United States Patent [19]
Cecchi et al.

[11] Patent Number: 6,013,119
[45] Date of Patent: Jan. 11, 2000

[54] FILTERING SYSTEM AND METHOD FOR INCUBATORS

[75] Inventors: Michael D. Cecchi, Madison, Conn.; Jacques Cohen, Mountain Lakes, N.J.; Brian Dale, Sorrento, Italy

[73] Assignee: Genx International, Inc., Madison, Conn.

[21] Appl. No.: 08/855,899

[22] Filed: May 15, 1997

[51] Int. Cl.[7] .............................. B01D 29/50; C12M 1/12
[52] U.S. Cl. ........................... 55/385.2; 55/467; 55/472; 55/486; 55/503; 435/303.1; 435/809; 261/121.1
[58] Field of Search ............................. 55/485, 486, 487, 55/482, 385.1, 385.2, 385.4, 467, 468, 472, 503, 505; 422/101; 435/303.1, 809; 261/121.1

[56] References Cited

U.S. PATENT DOCUMENTS

| | | |
|---|---|---|
| 3,057,138 | 10/1962 | Huxter . |
| 3,505,989 | 4/1970 | Truhan ..................................... 55/385.4 |
| 4,109,676 | 8/1978 | Price .......................................... 55/503 |
| 4,701,415 | 10/1987 | Dutton et al. ......................... 435/303.1 |
| 4,737,173 | 4/1988 | Kudirka et al. ............................ 55/472 |
| 5,047,348 | 9/1991 | Stinson ................................ 435/303.1 |
| 5,145,494 | 9/1992 | Sowinski ..................................... 55/486 |
| 5,360,469 | 11/1994 | Baron et al. ............................... 95/273 |
| 5,833,726 | 11/1998 | Kinkead et al. ......................... 55/385.2 |

FOREIGN PATENT DOCUMENTS

| | | | |
|---|---|---|---|
| 2924446 | 6/1979 | Germany ............................. 435/303.1 |
| 64-13985 | 1/1989 | Japan .................................. 435/303.1 |
| 1-285185 | 11/1989 | Japan .................................. 435/303.1 |
| 6-245753 | 9/1994 | Japan .................................. 435/303.1 |
| 6-245755 | 9/1994 | Japan .................................. 435/303.1 |

OTHER PUBLICATIONS

Ambient air and its potential effects on conception in vitro, Cohen, et al., Human Reproduction, vol. 12, No. 8, pp. 1742–1749, European Society for Human Reproduction and Embryology, 1997.

McGraw–Hill Encyclopedia of Science and Technology, vol. 2, 8th Edition, p. 244, 1997.

Primary Examiner—David A. Simmons
Assistant Examiner—Robert A. Hopkins
Attorney, Agent, or Firm—William W. Jones

[57] ABSTRACT

An improved filter system and method for filtering the gaseous environment of an incubator in which volatile organic compounds and particulate material are filtered from the gaseous environment. A filter is provided which includes a first filter medium to filter volatile organic compounds and a second filter medium to filter solid particulate material. A pump may be provided which draws a gas stream from the gaseous environment of the incubator and passes it through the filter. The pump and filter may be contained within a filter unit which may be used either internally or externally of the incubator.

30 Claims, 4 Drawing Sheets

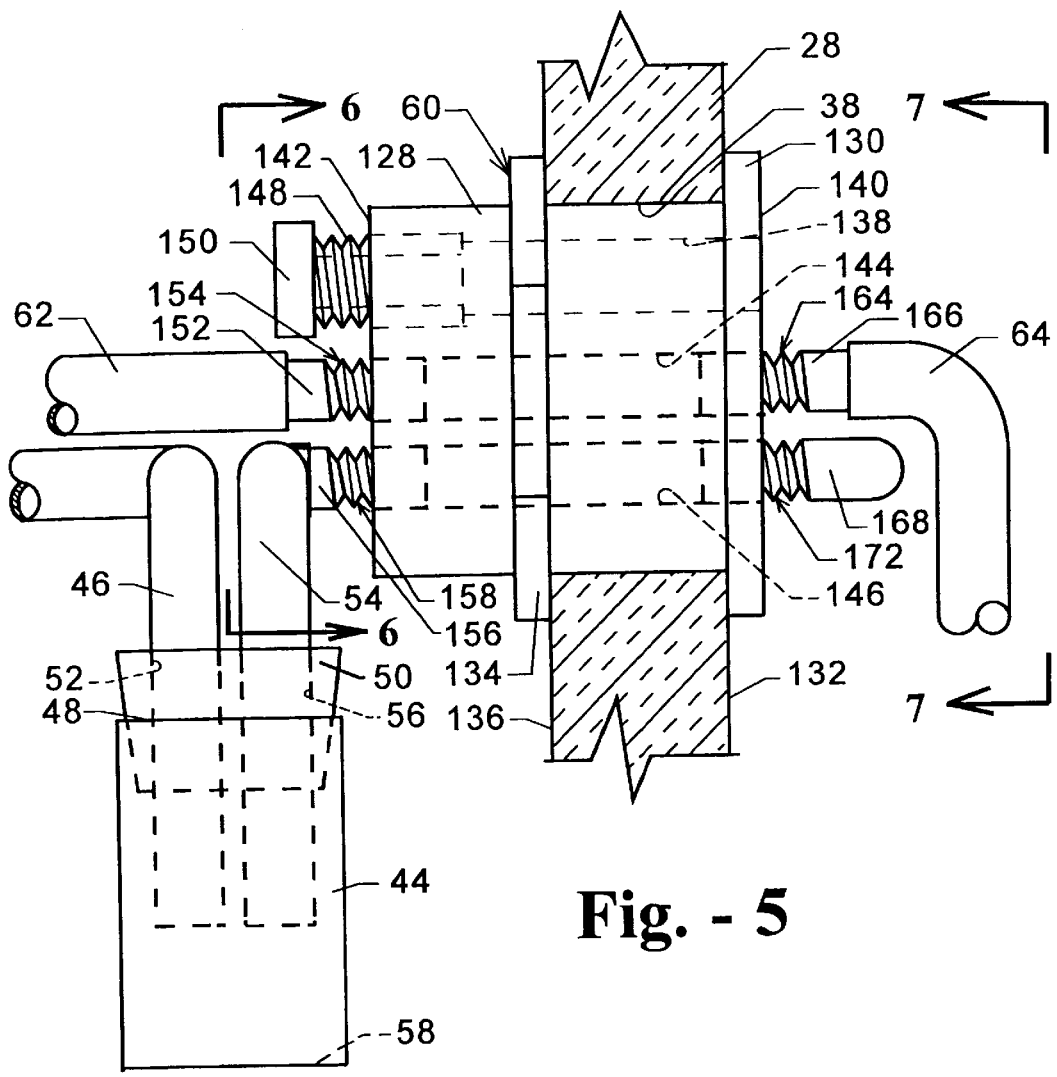
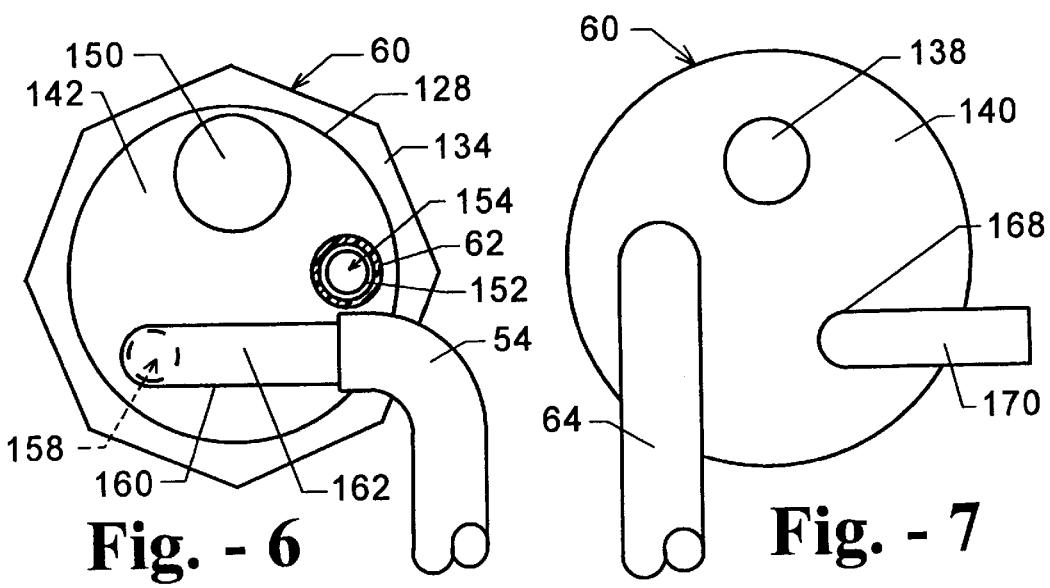

FILTERING SYSTEM AND METHOD FOR INCUBATORS

BACKGROUND OF INVENTION

1. Field of Invention

This invention relates generally to an improved filtering system and method. More particularly, this invention relates to an improved filtering system and method for incubators.

2. Background

Incubators provide an isolated and controlled environment for the maintaining of cells, tissues and various organisms in vitro during storage, manipulation and examination. Although it is known to filter the gaseous environment of the incubator to remove particulate materials, it has not been recognized that volatile organic compounds may be present within the incubator chamber which could have a deleterious effect on the samples within the chamber or on the process or manipulation being undertaken.

These undesirable volatile compounds may arise from a variety of sources and in a number of different ways. Such volatile compounds may be present in the atmosphere of the room in which the incubator is located and emanate from the gasing-off of many materials such as the glue used to set the tiles in the floor, fabrics present in the room and many other unsuspecting sources. When the incubator is opened, such undesirable volatile compounds will enter the incubator chamber. The supply of gases such as $CO_2$ and $O_2$ to the incubator environment from an external supply may be an unsuspected source of the undesirable volatile organic compounds.

Additionally it has been found that the materials used in the incubator for holding the specimens may be a source of such compounds. Sterile plastic ware such as used for petri dishes may off-gas styrene, ethyl-benzine and benzaldehyde. The media used in the culturing techniques such as mineral oil may also contribute to the unwanted volatile organic components.

While conventional incubators provide for airflow and filter out solid particulate material, none have recognized that there are sources of objectionable volatile organic compounds that may enter the incubator, or develop within the incubator, that should be filtered out to improve the quality of gaseous atmosphere of the incubator.

A controlled atmosphere enclosure is disclosed in U.S. Pat. No. 4,701,415. According to the disclosure of that patent there is a thermally insulated inner chamber containing a controlled gas atmosphere of carbon dioxide. The atmosphere of the inner chamber is drawn out, and the level of carbon dioxide is measure and increased if necessary. The carbon dioxide adjusted atmosphere is then filtered through a high efficiency particulate arresting (HEPA) filter to remove particulate and the filtered or non-particulate gas is then passed through a humidifier and returned to the inner chamber. This controlled atmosphere device only utilizes a HEPA filter. There is no recognition in this disclosure of the problem of gaseous impurities and no provision for their filtration.

Another controlled environmental chamber apparatus is disclosed in U.S. Pat. No. 5,169,217. The apparatus disclosed in this patent includes a chamber for maintaining biological material under controlled conditions of temperature and/or humidity having a door for controlling access to the chamber. A source of HEPA-filtered air flows downward in front of the door creating a curtain of air when the door is opened to prevent unclean air from entering the chamber. This disclosure also fails to recognize the problem of volatile organic contaminants and the desirability of their filtration.

U.S. Pat. No. 5,352,414 discloses an incubator unit and filter system for performing radioactive experiments. According to the disclosure of this patent, the chamber is provided with static filters and the gas exhaust line is provided with an exhaust filter. According to the patent, the gas used in the incubator environment is flushed through the chamber and exits through the exhaust filter. After flushing, the chamber is sealed off during the experimentation period. After the experiment, the chamber is flushed again to remove the contaminating gases and volatiles. According to the disclosure of this patent, during the experiment, radioactive active gases or other contaminants will be released into the chamber and will tend to be picked up by the charcoal paper sheets. This patent is especially concerned with radioactive gases. There is no recognition of the problem of undesirable volatile organic compounds. Additionally, there is no recognition of the desirability for recirculating the gaseous environment of incubator to filter the volatile organic compounds from the gaseous environment.

SUMMARY OF THE INVENTION

In view of the above, it is an object of the present invention to provide an improved filtering system and method for an incubator.

A more specific object of the present invention is to provide an improved filtering system and method for an incubator which will filter volatile organic compounds.

Another object of the present invention is to provide an improved filtering system for incubators which may be retrofitted to existing incubators.

These and other objects and advantages may be achieved in accordance with one aspect of the present invention through the provision of a filter system for an incubator for filtering the gaseous environment within said incubator, said incubator having a recirculating gas path for recirculating a gas stream from said gaseous environment, said filter system comprising an inlet in said recirculating gas path for receiving a recirculating gas stream from the gaseous environment of the incubator; an outlet in said recirculating gas path for returning the recirculating gas stream to said gaseous environment of said incubator; and a volatile organic compound-removing filter medium located between said inlet and said outlet for filtering said recirculating gas stream, said volatile organic compound-removing filter medium serving to filter volatile organic compounds from said recirculating gas stream.

In accordance with another aspect of the present invention, there is provided a filter system for an incubator for filtering volatile organic compounds and particulate material from the gaseous environment within the incubator comprising an inlet for receiving a gas stream from the gaseous environment of the incubator; an outlet for returning the gas stream to gaseous environment of the incubator; and a filter connected between said inlet and said outlet for filtering said stream of gas, said filter serving to filter volatile organic compounds and particulate material from said gas stream.

According to another aspect of the present invention, there is provided a filter unit for use in filtering volatile organic contaminants and solid particulate material from the gaseous environment within an incubator comprising a housing; a partition dividing said housing into first and second compartments; a pump located in said first compartment; a filter located in said second compartment; an electrical power connector extending from said pump through said housing to a point external of said housing; said housing having an inlet port to provide for the inflow of a gaseous stream from the interior environment of an incubator into the filter unit and an outlet port for providing of the outflow of filtered gas stream from the filter unit to the interior of the incubator; and said pump and said filter being connected between said inlet port and said outlet port so that said pump causes the flow of the gaseous stream into said inlet port through said pump and filter and through said outlet port to said incubator.

According to a further aspect of the invention, there is provided a connection device for mounting in the wall of an incubator for permitting access from the outside to the interior of said incubator for components of a filtering system for filtering volatile organic compounds and particulate material from the gaseous environment within the incubator comprising a body member for mounting in the wall of said incubator and having an outer face exposed to the outside and an inner face exposed to the inside of said incubator; a first bore extending through said body between said two faces; a fitting attached to said outer face communicating with said first bore to provide an outlet port for a gas stream from the interior of said incubator; a second bore extending through said body between said two faces; a fitting attached to said outer face communicating with said second bore to provide an inlet port for a filtered gas stream to the interior of said incubator; and a fitting attached to said inner face in communication with said second bore to provide a port for connection of tubing to direct the flow of the filtered gas steam within the incubator.

According to yet another aspect of the present invention, there is provided a continuous process for filtering volatile organic compounds and particulate material from the gaseous environment of an incubator comprising drawing a gas stream from the gaseous environment of the incubator; reducing the amount of humidity in the drawn gas stream; passing the moisture-reduced gas stream to a filter which filters volatile organic compounds and solid particulate material from said gas stream; introducing the filtered gas stream back into the gaseous environment while continuing to draw off a gas stream; and repeating steps a through d to provide said continuous process.

According to still further aspect of the present invention, there is provided a filter system for use with an incubator having a supply of gas fed to the interior of said incubator from an external storage source, said filter system comprising a flow path for said gas from said source to the interior of said incubator, and a filter connected between said storage source and the interior of said incubator for filtering said gas, said filter serving to filter volatile organic compounds and particulate material from said gas stream.

The present invention may be better understood by reference to the following detailed description and to the accompanying drawings in which:

BRIEF DESCRIPTION OF THE DRAWINGS

FIG. 5 is an enlarged view through a section of the wall of an incubator showing a connector device used when the filter unit is external of the incubator;

FIG. 6 is a partial elevational view, partially in section, taken in the direction of the lines 6—6 of FIG. 5 and showing the outside face of the connector device of FIG. 5.

FIG. 7 is a partial elevational view taken in the direction of the lines 7—7 of FIG. 5 and showing the outside face of the connector device of FIG. 5;

DETAILED DESCRIPTION

Figure 1:
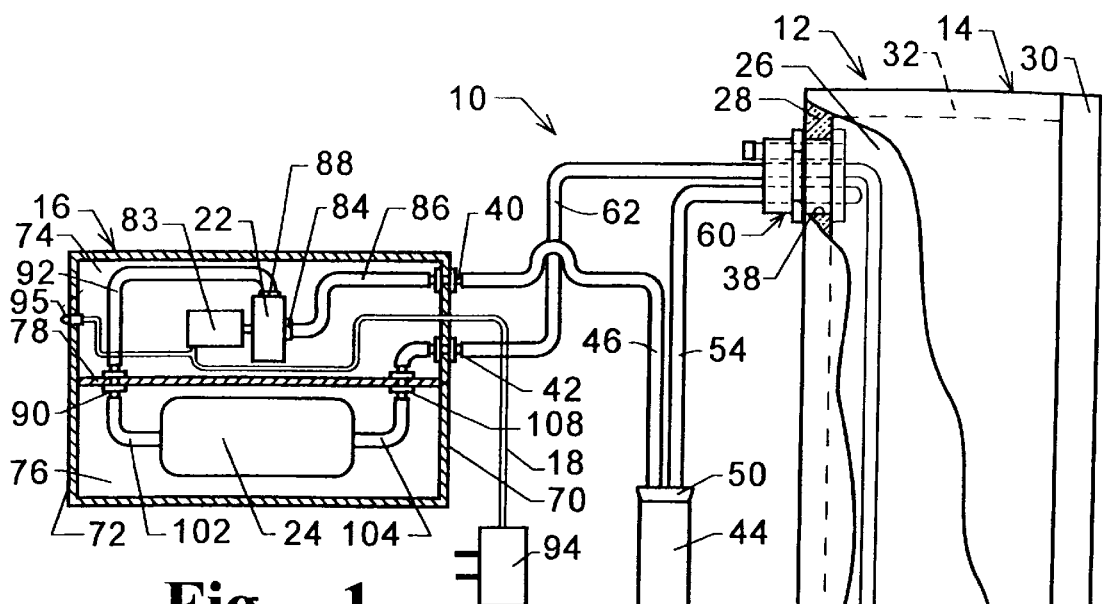
FIG. 1 is a schematic diagram of a filtering system for an incubator according to the present invention with the filter unit provided outside of the incubator.
Figure 2:
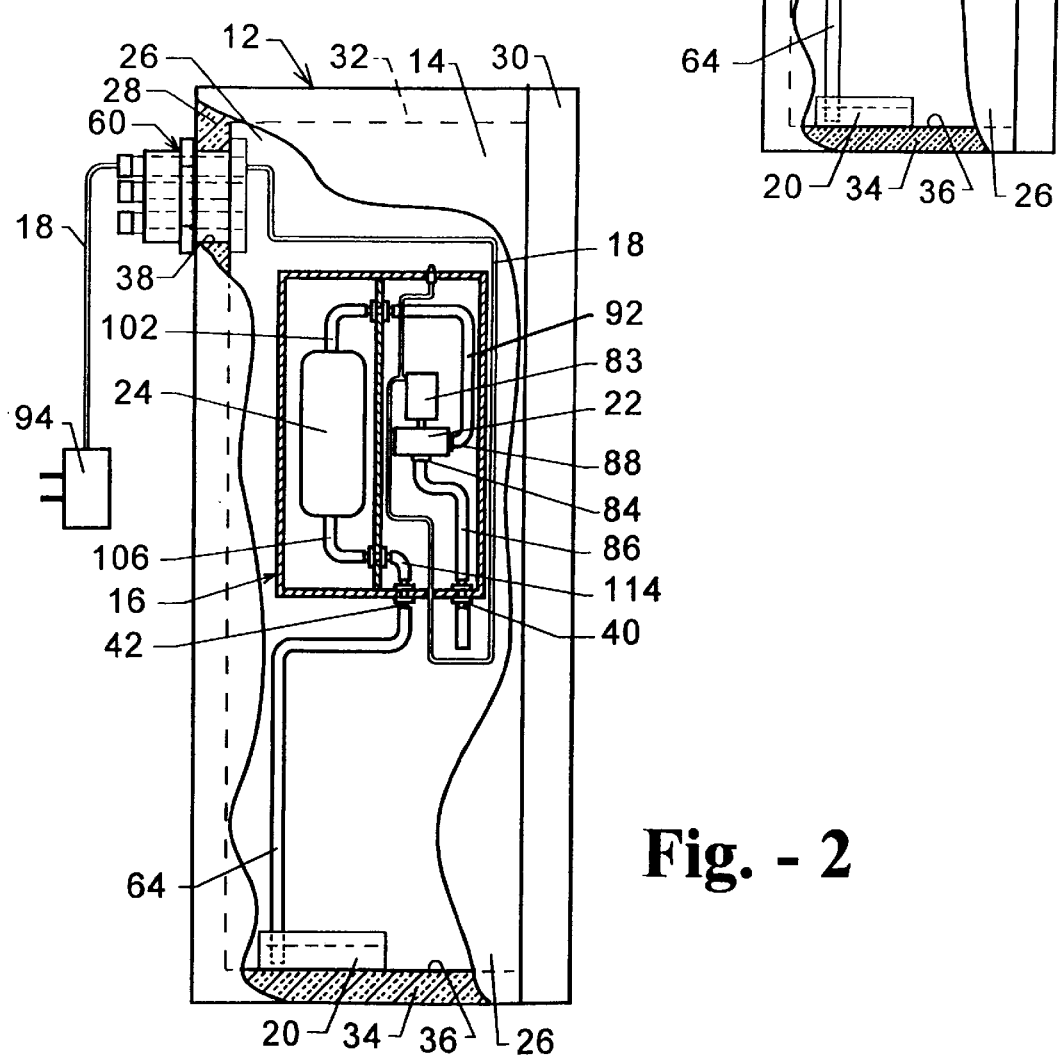
FIG. 2 is a schematic diagram of a filtering system for an incubator according to the present invention with the filter unit mounted with the incubator.

Referring to the drawings, and particularly FIGS. 1 and 2, the filtering system 10 of the present invention may generally include an incubator 12 having a cabinet or enclosure 14, a filter unit 16, a power connector or cord 18 attached to the filter unit 16, and a water pan or reservoir 20 within the incubator cabinet 14 to which the recirculating air from the filter unit 16 is fed. The filter unit 16 contains an electrical pump 22 and a filter 24.

More specifically, the incubator 12 may be any of the various commercially available units of the type customarily used to isolate test samples and cultures in a controlled environment. Such incubators 12 provide a chamber with a controlled environment for maintaining cells, tissues and organisms in vitro during storage, manipulation and examination. As shown in FIGS. 1 and 2, the incubator 10 may include the cabinet 14 defined by two opposed side walls 26, a rear wall 28, a front wall 30 including an access door (not shown), and a top 32 and bottom 34. The water pan or reservoir 20 may be provided internally of the cabinet 14 on a shelf (not shown) or bottom surface 36. The rear wall 28 may be provided with an aperture 38 which, in use, may be plugged or used to provide an entrance for gases from an external source.

In the embodiment shown in FIG. 1, the filter unit 16 is located outside the incubator cabinet 14. The filter unit 16 has an unfiltered air inlet port 40 and a filtered air outlet port 42. The unfiltered air inlet port 40 is connected to a moisture collector or moisture trap 44 by an incoming air line 46. As shown most clearly in FIG. 5, the moisture trap 44 may be a suitable container of non-toxic material having an open top 48 in which is secured a silicone stopper 50 having an aperture 52 through which the incoming air line 46 passes. An outflow air line 54 from the incubator 10 also extends through an aperture 56 in the stopper 50 into the moisture collector 44. As will be noted in FIG. 5, both the incoming air line 46 and the outflow air line 54 terminate short of the bottom 58 of the moisture collector 44. The outflow air line 54 is connected through a connector device 60 in the wall of the incubator 12 to the interior of the incubator cabinet 14.

A filtered air outflow line 62 is attached to the filtered air outlet port 42 of the filter unit 16 and extends to the connector device 60. The connector device 60 connects the line 62 with an in-going filtered air tube 64 which extends from the connector device 60 to the water reservoir 44.

Figure 3:
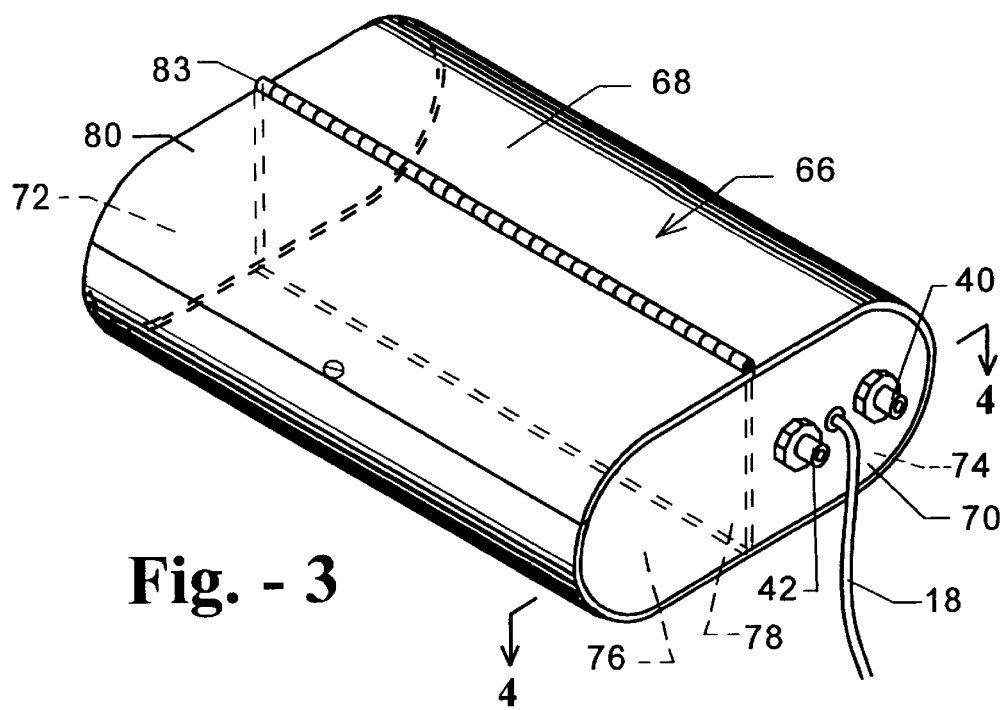
FIG. 3 is an enlarged isometric view of the filter unit.

As shown in FIGS. 1 and 3, the filter unit 16 is a self-contained, free-standing unit and comprises a housing 66 including a main body 68, a connector end 70 in which the unfiltered air inlet port 40 and filtered air outlet port 42 are located, and an indicator end 72. The sides of the housing 66 are generally semi-circular as shown. The housing 66 is divided into a first and a second compartment, 74 and 76 respectively, by an internal longitudinally extending partition 78. A door 80, hinged to the main body 68 at hinge point 82, is provided over the second compartment 76 to provide access thereto. The door 80 and main body 68 completely encircle the perimeter of the ends 70 and 72 to form an enclosed unit when the door 80 is closed. The housing 66, including the ends 70 and 72, partition 78, body 68 and door 80 are all preferably fabricated from stainless steel, although other materials such as non-toxic plastics may be used including Teflon, polypropylene, PETG, and hard silicon.

Referring particularly to FIGS. 1 and 3, the pump 22, along with its associated motor 83, is mounted in the first compartment 74 of the filter unit 16. The intake port 84 of the pump 22 is connected to the unfiltered air inlet port 40 by suitable tubing 86. The discharge port 88 of the pump 22 is connected to a connector 90 in the partition 78 by suitable tubing 92. The electrical power cord 18 extends from the pump motor 83 through the connector end 70 of the housing 66 and terminates externally of the filter unit 16 in an power plug 94 for connection to a suitable power source. The power plug 94 may include a suitable converter for converting the 120 volt AC power supply to a 12 volt DC current. The power cord 18 also extends to an indicator light 95 mounted in the indicator end 72 of the housing 66. The light 95, when on, provides an indication that the filter unit 16 is connected to the external power source and the unit is energized.

The filter 24 is mounted in the second compartment 78 of the filter unit 16 and may be in the form of a filter cartridge 96. The cartridge 96 includes a generally cylindrically shaped main body casing 98 in which the filter medium is located. An inlet port 100 at the inlet end of the body casing 98 has one end of an L-shaped inlet tube 102 connected thereto. The other end of the inlet tube 102 is connected to the connector 90. An L-shaped filtered air outlet tube 104 has one end connected to an outlet port 107 in the outlet end of the body casing 98 and has its other end connected to a connector 108 in the partition 78 of the filter unit 16. The outlet side of the connector 108 is connected to the filtered air outlet port 42 in the connector end 70 of the housing 66 by a tube 109.

Each of the connectors 90 and 108 is a spring biased, quick connect/disconnect, type connector which prevents flow therethrough when the filter cartridge 96 is not attached. The connectors 90 and 108 each include a bore 110 in which a reduced end portion 112 of a respective L-shaped inlet tube 102 or outlet tube 104 is received. When the reduced end portion 112 of the tube 102 or 104 is inserted in bore 110, it moves an internal valve sleeve 114 in the connector 90 or 108 against a spring bias to permit flow through the respective connector 90 or 108. The inlet tube 102 and outlet tube 104 are held in place in their respective connectors 90 and 108 by a spring biased detent member (not shown). Upon release of the detent members, the spring bias moves each valve sleeve 114 into its shut-off position and ejects the end portions 112 of the tubes 102 and 104 out of the bores 110. By using a quick connect/disconnect coupling for attaching the filter cartridge 96 to the flow path of the recirculating air in the filter unit 16, the filter cartridge 96 may be easily replaced when necessary. In addition, the automatic flow shut off of the connectors 90 and 108 prevents external air from entering the system when the filter cartridge 96 is removed.

Figure 4:
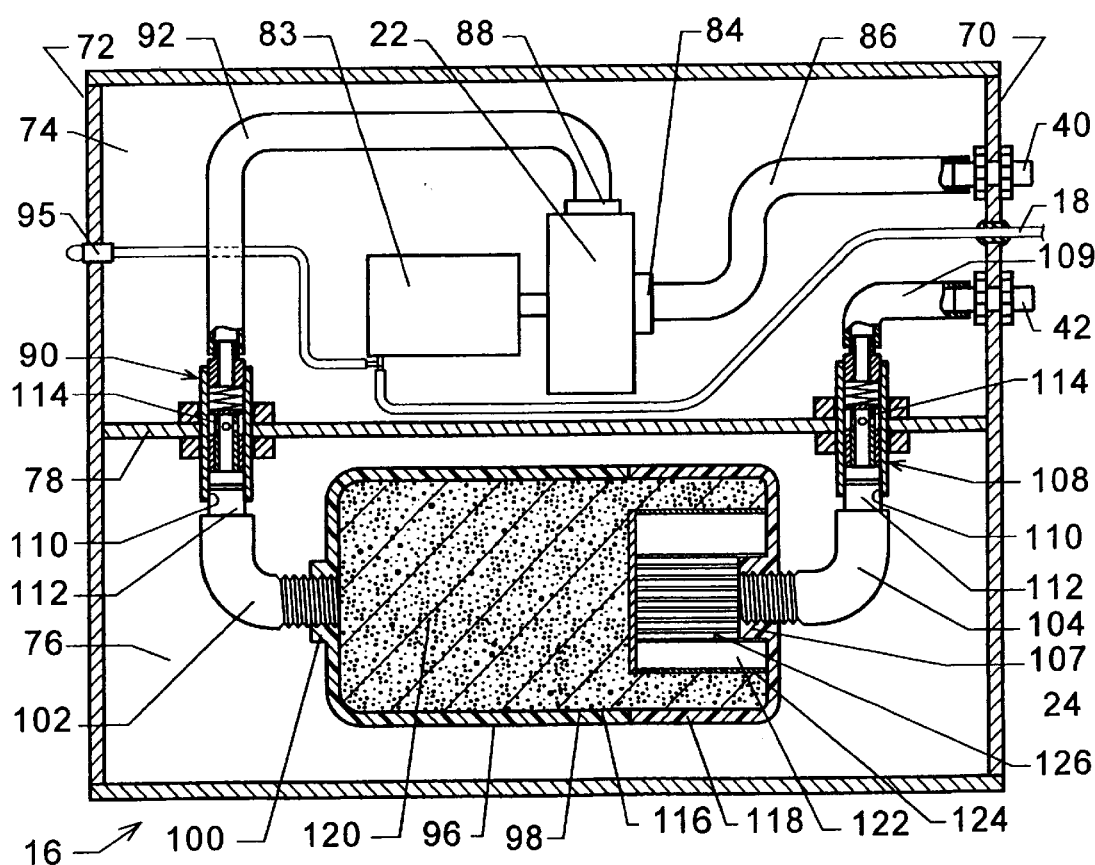
FIG. 4 is a sectional view of the filter unit taken along the lines 4—4 of FIG. 3.

The filter cartridge 96 is shown in more detail in FIG. 4. The casing 98 of the filter cartridge 96 is generally cylindrical in shape and includes an first portion 116 which includes the inlet port 100 to which the inlet tube 102 is connected and a second portion 118 which includes the outlet port 108 to which the outlet tube 104 is connected. Within the interior of the casing 98, the first portion 116 includes a first volatile organic compound-removing filter medium 120 which serves to filter and remove the undesirable volatile organic compounds. By way of example, the various volatile hydrocarbons which may be filtered by the first filter medium include alkanes, hexanes, benzenes, propenes, ethers, xylenes, methanes and combinations thereof, and the like in gaseous or vapor form. By way of example. the first medium may be untreated carbon, activated carbon, activated charcoal, and combinations thereof, although other materials capable of filtering out the materials listed may be used.

The second portion 118 of the interior of the casing includes a second particulate material-removing filter medium 122 in the form of a hollow cylinder co-axial with the outlet port 108 and positioned against the bottom of the casing 98. The second filter medium 122 is selected to filter out particulate material in the gas stream passing therethrough. Preferably, this medium is a high efficiency particulate arresting (HEPA) filter media although other suitable filter media may be used such as non-woven filter media. The second filter medium 122 may be in the form of a pleated filter element having a cylindrical outer periphery 124 and an axially extending cylindrical bore 126. Examples of particulate material to be filtered out include airborne solid particles, pollen, plastic particles and rust particles, as well as particles from the first filter medium.

The first filter medium 120 extends downward in the casing 98 and surrounds the cylindrical second filter medium 122. This ensures that the gas stream passes though both filter media. If the cylindrical second filter medium 122 was not surrounded by material of the first filter medium 120, the gas stream could pass along the inner wall of the casing 98 and through the second medium 122 without having passed through the first medium 120.

The pump 22 may be any suitable commercially available unit preferably operated by a 12 volt DC current. The pump 22 may be any suitable commercially available unit preferably operated by a 12 volt DC current and having a relative low flow rate. In the case where the filter unit 16 is located external of the incubator 12, the flow rate of the pump should be sufficiently low to ensure that excess humidity is not pulled into the system from the moisture trap 44. High flow rates will cause excessive condensation which will be drawn into the filter. Also, the flow rate must be low enough to ensure that the air stream has enough residence time in the filter to maximize the filtering of the contaminants.

With the present arrangement, in the case of the filter unit 16 being used outside of the incubator 12, the flow rate should be equal to or less than about 0.3 liters per minute and preferably between about 0.1 and 0.3 liters per minute. In the case where the filter unit 16 is located within the incubator 12, the flow rate of the pump 22 may be higher, up to about 3.0 liters per minute. However, if it is desired that the filter unit 16 have universal application, the flow rate of the pump 22 should be that for an external unit.

The connector device 60 is mounted in the aperture 38 in the wall 28 of the incubator cabinet 14 to provide a connection for the filter unit 16 between the inside and outside of the incubator 12. The connector device 60, in the embodiment where the filter unit 16 is located external of the incubator cabinet 14 is shown particularly in FIGS. 5–7. The connector device 60 includes a cylindrical body 128 having a flange 130 on its inner end. The cylindrical body 128 extends through the aperture 38 in the wall 78 of the incubator cabinet 14 with the flange 130 positioned against the inner surface 132 of the wall 78 as shown in FIG. 5. The aperture 38 may be one that is normally provided in the rear wall 78 of commercially available incubators for the purpose of introducing extra gases into the interior of the incubator, but which, in many applications, is not used. Alternatively, another apertures may be provided in the one of the walls of the incubator 12. A tightening nut 134 is threaded onto the outer surface of the cylindrical body 128 and tightened against the outside surface 136 of the wall 78 of the incubator cabinet 14 to secure the connector device 60 within the wall 78.

A first aperture or bore 138 is provided through the body 128 extending from an inner face 140 to an outer face 142 of the connector 60. The axis of this aperture 138 may lie in a vertical plane passing though the axis of the cylindrical body 128 and in a horizontal plane positioned above a horizontal plane passing though the axis of the cylindrical body 128.

A second aperture or bore 144 extends through the cylindrical body 128 between the inner and outer faces 140 and 142 and is positioned such that its axis lies in a vertical plane which is parallel to, but offset to one side with respect to, the vertical plane passing though the axis of the cylindrical body 128 . The horizontal axis containing the plane of the second aperture 144 may be co-planar with the horizontal plane of the axis of the cylindrical body 128.

A third aperture or bore 146 extends though the cylindrical body 128 of the connector device 60 between the inner and outer faces 140 and 142. The axis of the third aperture 146 may be in a horizontal plane positioned below the horizontal plane containing the axis of the cylindrical body 128. The vertical plane containing the axis of the third aperture 146 may be parallel to, but offset to the side opposite the second aperture from, the horizontal plane containing the axis of the cylindrical body 128.

An externally threaded fitting 148, such as a threaded nipple, is threaded into the outer face 142 of the body 124 coaxial with the first aperture 138. In the case where the filter unit 16 is positioned external of the incubator cabinet 14, this aperture 138 may be plugged by providing a screw cap 150 on the free end of the fitting 148. Alternatively, a plug may be provided in the end of the fitting 148.

A fitting 152, such as a push to connect tube fitting, having a threaded end portion is threaded into the second aperture 144 and extends from the outer face 142 of the cylindrical body 128. This fitting 152 provides an inlet port 154 to which the filtered air outflow line 62 from the filter unit 16 is connected.

Another fitting 156 having a threaded end portion is threaded into the third aperture 146 and extends from the outer face 142 of the cylindrical body 128. This fitting 156 provides an outlet port 158 for the gas stream from the interior of the incubator cabinet 14. An elbow 160 may be connected to the fitting 156 which includes a horizontally extending portion 162 extending parallel to the outer face 142 of the body 128. The outflow air line 54 to the moisture collector 44 is connected to the free end of the elbow 160.

On the inner face 140 of the cylindrical body 128, a fitting 164, such as a push to connect tube fitting, having a threaded end portion is threaded into the second aperture 144. This fitting 164 provides a outlet port 166 for the connector device 60 to which the in-going filtered air tube 64 to the water reservoir 20 is connected.

Also provided on the inner face 140 of the cylindrical body 128 is an angled or L-shaped tube 168 having a threaded end which is threaded into to the third aperture 146 in a manner such that tube 168 includes a straight portion 170 extending horizontally in a direction parallel to the inner face 140. The tube 168 provides an inlet port 172 for the gas stream from the interior of the incubator cabinet 14 to enter the bore 146 in the connector device 60 and pass out of the connector device 60 though the port 158 into the outflow air line 54 to the moisture trap 44.

In operation of the embodiment as shown in FIGS. 1 and 5–7, wherein the filter unit is located outside of incubator cabinet 14, the filter system 10 is energized by connecting the plug 94 of the power cord 18 to a suitable external power source such as a 112 volt outlet. The pump 22 then draws a gas stream from the interior of the incubator 10 into the tube 168 connected to the bore 146 in the connector device 60. The gas stream passes through the connector device 60, out of the port 158 into the outflow air line 54 to the moisture trap 44. This trap 44 will collect any moisture in the gas stream that may have formed due to change in temperature and pressure of the gas stream at this point as compared with the temperature and pressure within the incubator 12.

The gas stream exits the moisture trap 44 thorough the incoming air line 46 and passes to the input port 40 of the filter unit 16. The gas stream enters the filter unit 16 and is drawn into the intake port 84 of the pump 22 and then discharged from the discharge port 88 into the line 92 where it passes through the connector 90 in the partition 78, through line 102, into the filter 24. The gas stream is forced though both filter media 120 and 122 within the filter cartridge 96 so that volatile organic compound and particulate materials are filtered out of the gas stream.

The filtered gas stream exits the filter 24 and passes through the connector 108 in the partition 78 in the filter unit 16, through outlet tube 109 and exits the filter unit 116 through the outlet port 42. The filtered gas stream then passes though the filtered gas outflow line 62 to the inlet port 154 of the connector device 60. The filtered gas stream exits the connector device 60 though the port 164 into the incoming filter gas tube 64 to the water reservoir 20. The filtered gas stream bubbles up through the water in the reservoir 20 which serves to add humidity to the incoming filtered gas stream. If additional humidity is not necessary, the water reservoir 20 may be omitted. As long as the pump 22 is running, a gas stream is continuously removed from the incubator 10, filtered and returned to the incubator 10 so that the gaseous environment with the incubator is being continuously filtered.

Figure 8:
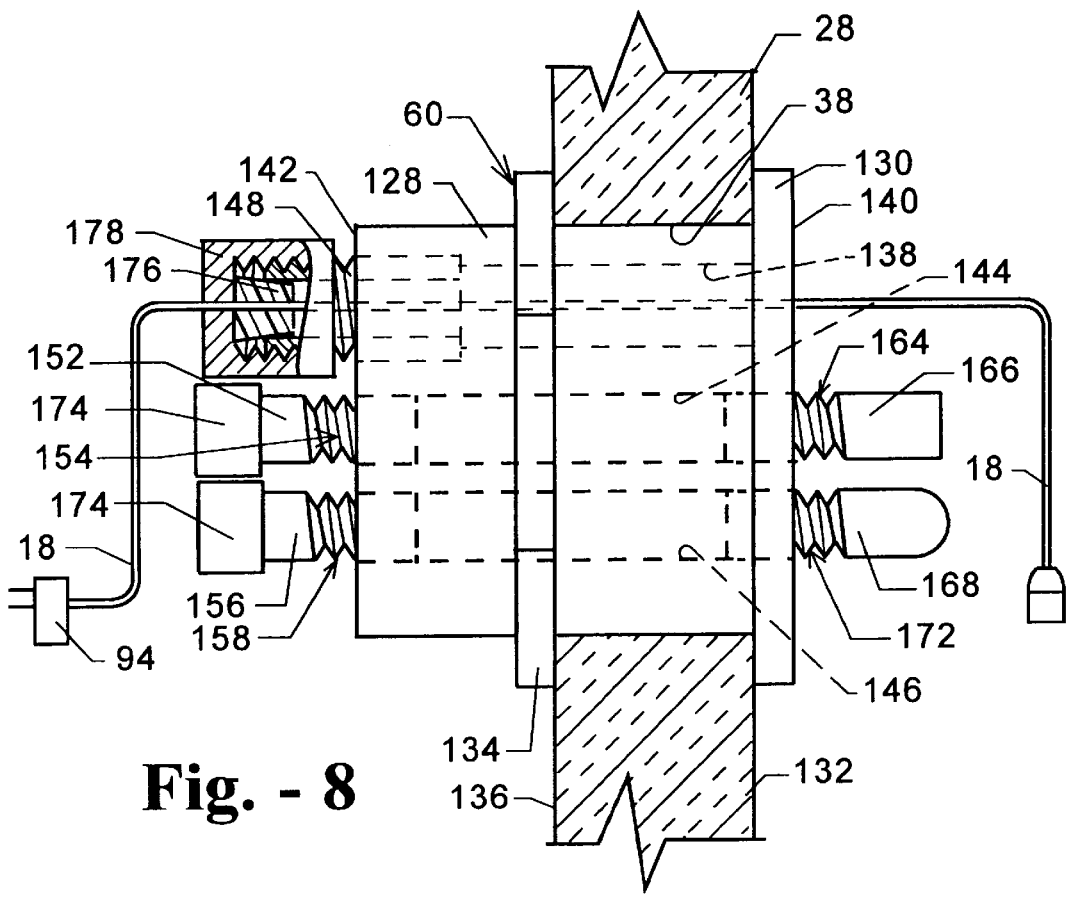
FIG. 8 is an enlarged view similar to that of FIG. 5, but showing the connector device when the filter unit is located internally of the incubator.

In the embodiment shown in FIGS. 2 and 8, the filter unit 16 is mounted or contained within the incubator cabinet 14. In this case, the connector device 60 serves to provide a passage for the electrical cord 18 from the filter unit 16 located in the incubator 10 to a power supply located external of the incubator 10. The ports 154 and 158 of the connector device 60 may be plugged by suitable caps 174 or other means as they are not used in this case. The power cord 18 extends through the first aperture 138 in the connector device 60 and passes out through the fitting 148. A silicone stopper 176 is provided about the cord 18 and is inserted into the end of the fitting 148 as shown in FIG. 8. A screw cap 178, through which the power cord 18 may extend, is attached to the end of the fitting 148 to hold the stopper 176 in place and provide a tight seal about cord 18.

The operation of the system of this embodiment is essentially the same as the system shown in FIGS. 1 and 5–7. However, in this case, since the filter unit 16 is within the incubator cabinet 14, there is no need for the moisture collector 44.

With the plug 94 connected to an external power supply, and the system energized, the gaseous stream from the gaseous environment in the incubator 10 in drawn into the filter unit 16 though the input port 40 by the pump 22. The gas stream passes from the input port 40 to the intake port 84 of the pump 22 and is discharged therefrom though the discharge port 88 to the connector 90 in the partition 78. The gas stream passes through the connector 90 to the inlet port 100 of the filter 24. The gas stream is forced though both the filter media 120 and 122 within the filter 24 so that volatile organic compounds and particulate materials are filtered out of the gas stream.

The filtered gas stream exits the filter 24, passes through the connector 108 in the partition 78 in the filter unit 16, and exits the filter unit 116 through the outlet port 42. The line 64 to the water reservoir 20 is connected directly to the outlet port 42 of the filter unit 16 so that the gas stream, upon exiting the filter unit 16, passes to the water reservoir 20 and then into the gaseous environment of the incubator 10.

With the above arrangements, an effective filtering system is provided for the continuous filtering of volatile organic compounds and particulate material from the gaseous environment of an incubator.

By way of example, a prototype system for testing purposes was set up which included a commercial incubator and a pump, external of the incubator, and having its intake connected by tubing to the interior of the incubator. The discharge end of the pump was connected to the inlet of a filter consisting of packed carbon granules in a glass tube. The outlet of the filter was connected by tubing to a pan of water within the incubator. The pump had a flow rate of 0.1 liters per minute. Various sources of volatile organic compounds were placed in the incubator. The air in the incubator was tested for concentrations of various volatile organic compounds before and after the test unit was run. The following Table 1 shows the level of various volatile organic compounds before and after filtering.

TABLE 1

| Compound | Pre-filtered Concentration (micro-grams/meter$^3$) | Poat-filtered Concentration (micro-grams/meter$^3$) |
|---|---|---|
| Enflurane | 200 | 100 |
| Acetone | 39 | 32 |
| C-9 Branched Alkane | 100 | 20 |
| Methylcyclohexane | 50 | 20 |
| n-Decane | 85 | 14 |
| C-8 Branched Alkane | 60 | 10 |
| C-11 Branched Alkane | 50 | 10 |
| C-11 Branched Alkane | 50 | 9 |
| Decahydro-2-Methylnaphthalene Isomer | 40 | 9 |
| Toluene | 21 | 4.8 |
| Nonane | 34 | 4.4 |
| Carbon Disulfide | 4.0 | 4.3 |
| Styrene | 45 | 3.0 |
| Chloromethane | 2.7 | 2.6 |
| Benzene | 8.0 | 2.5 |
| Methylene Chloride | 2.4 | 2.4 |
| 1,1,1-Trichloroethane | 1.5 | 1.2 |
| Octane | 8.8 | 1.2 |
| Chloroform | 0.85 | 1.2 |
| Tetrachloroethane | 1.2 | 0.93 |
| Carbon Tetrachloride | 1.0 | 0.84 |
| n-Hexane | 3.1 | 0.83 |
| Trichlorotrifluoroethane | 1.2 | 0.81 |
| tert-Butyl Methyl Ether | 4.3 | 0.72 |
| 1,2,4-Trimethylbenzene | 2.4 | 0.70 |

As shown by the table, the using a filter system as contemplated by this invention significantly reduced the level of volatile organic compounds in the gaseous environment.

Figure 9:
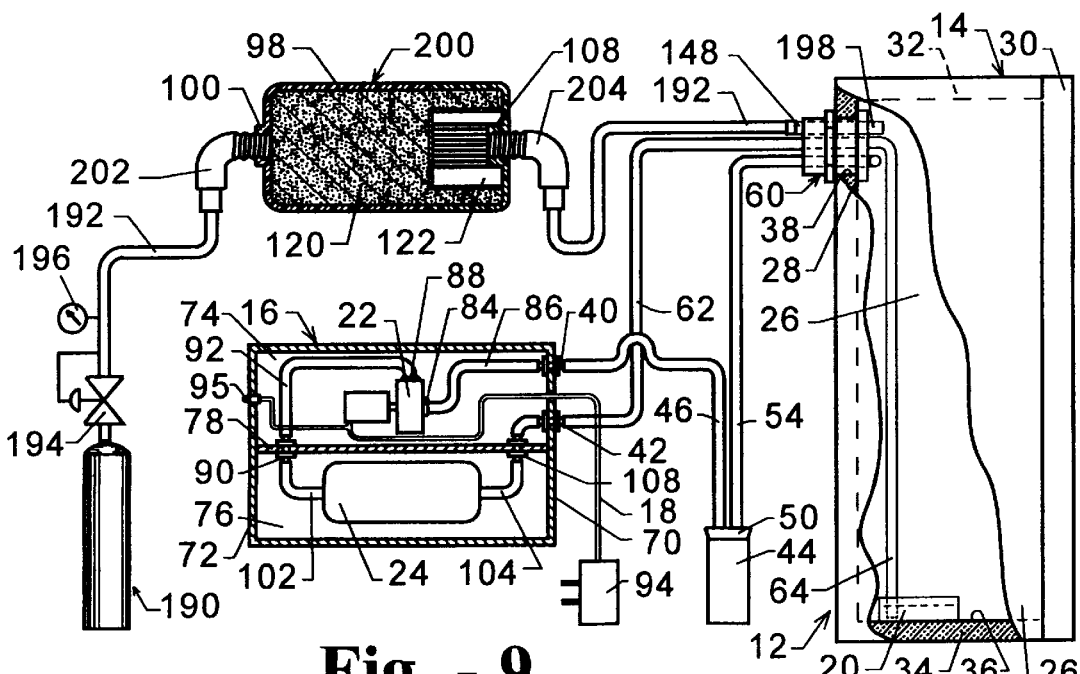
FIG. 9 is a schematic diagram of another application of the filter of the present invention.

Referring to FIG. 9, another embodiment of the present invention is shown in which the interior of the incubator 12 is provided with a gas from an external storage source. The source of gas may be a suitable tank or canister 190 containing the desired gas under pressure and located external of the incubator 12. Typically, such tanks 190 may be located a distance away from the incubator 12, even in another room, and are connected to the incubator by suitable connector tubing 192. As is conventional, the outlet of the tank 190 may be connected to the connector tubing 192 through a pressure regulator 194, with a pressure gauge 196 downstream of the regulator 194. Examples of gases that may be introduced into the incubator 12 from an external storage source include oxygen, carbon dioxide and nitrogen. The specific gas introduced into the incubator 12 at any given time depends upon the type of experiment or procedure being performed within the incubator 12.

In the embodiment shown in FIG. 9, the filter unit 16 is shown being used to filter a gas stream from the gaseous environment of the interior of the incubator 12 as described in connection with FIG. 1. As previously described, a gas stream from the interior of the incubator 12 is directed through the moisture trap 44 and the filter unit 16 and returned to the interior of the incubator 12.

The tank 190 containing the gas to be introduced into the incubator 12 is connected to the incubator 12 by the connector tubing 192. The connector tubing 192 is connected at its outlet end to the fitting 148 in the outer face 140 of the connector 60 in the wall 28 of the incubator 12. As shown in FIG. 5, the fitting 148 communicates with the first bore 138 in the connector 60. A short tube 198 or other type of fitting may be provided on the inside face 140 of the connector 60 in communication with the first bore 138 to direct the incoming gas within the incubator 12.

A filter 200 is mounted in the line 192. The filter 200 is substantially the same as the filter 24 used in the filter unit 16. The filter 200 includes the main body casing 98 as heretofore described having the inlet port 100 and the outlet port 108. The filter 200 also includes the first filter medium 120 which serves to filter and remove undesirable volatile organic compounds and the second filter medium 122 which filters out particulate material as described above.

The inlet port 100 of the filter 200 has connected thereto a suitable connector 202 to which the line 192 from the tank 190 is connected. The outlet port 108 of the filter 200 has a similar type connector 204 connected thereto to which the line 192 to the connector 60 is attached. With the provision of the filter 192 of the type of the present invention as described, the incoming gas to the incubator 12 is filtered to filter out unwanted volatile organic compounds which may be present in the gas within the tank and also will filter out solid particulate material such as solid sediment or rust that may have accumulated in the tank 192.

While the filter 200 is shown in FIG. 9 as being used simultaneously with the filter unit 16, the filter 200 may be used alone to filter the external gas supply even when the filter unit 16 is not used. In FIG. 9, the filter 200 is shown connected in the external connector tubing 192. Alternatively, the filter 200 may have its outlet port 108 connected directly to the connector 60 by a suitable fitting, with the end of the tubing 192 connected to the inlet port 100. As additional alternatives, the filter 200 may be mounted on the outside of the incubator cabinet 14, or positioned inside the cabinet 14 and connected by suitable tubing passing though the wall of the cabinet 14 from the filter 200 to the tank 192, with the incoming gas being released from the outlet 108 of the filter 200 into the interior of the incubator. Although the invention has been described above with reference to specific embodiments thereof, it is apparent that many changes modifications and variations can be made without departing from the concept disclosed herein. Accordingly, it is intended to embrace all such changes, modifications, and variations that fall within the scope of the appended claims.

What is claimed is:

1. A filter system for an incubator for filtering the gaseous environment within said incubator, said incubator having a recirculating gas path containing a recirculating pump for recirculating a gas stream from said gaseous environment, said filter system comprising:
   a. an inlet in said recirculating gas path for receiving a recirculating gas stream from the gaseous environment of the incubator;
   b. an outlet in said recirculating gas path for returning the recirculating gas stream to said gaseous environment of said incubator; and
   c. a volatile organic compound-removing filter medium located between said inlet and said outlet for filtering said recirculating gas stream, said volatile organic compound-removing filter medium serving to filter volatile organic compounds from said recirculating gas stream.

2. The filter system of claim 1 further including a particulate material-removing filter medium connected between said inlet and said outlet for filtering said recirculating gas stream, said particulate material-removing filter medium serving to filter particulate material from said recirculating gas stream.

3. The filter system of claim 2 wherein said volatile organic compound-removing filter medium is selected from the group consisting of untreated carbon, activated carbon, activated charcoal and combinations thereof, and wherein said particulate filter medium is selected from the group consisting of HEPA and non-woven filter media.

4. The filter system of claim 2 further comprising a filter unit, said volatile organic compound-removing medium and said particulate material-removing filter medium being mounted in said filter unit and forming a self-contained structure.

5. A filter system for an incubator for use in filtering volatile organic compounds and particulate material from a gaseous environment within the incubator, said filter system comprising:
   a. an inlet for receiving a gas stream from the gaseous environment of the incubator;
   b. an outlet for returning the gas stream to the gaseous environment of the incubator;
   c. a filter assembly interposed between said inlet and said outlet for filtering said gas stream, said filter assembly including a first filter medium serving to filter volatile organic compounds from said gas stream and a second filter medium serving to filter particulate material from said gas stream; and
   d. a pump operable to circulate said gas stream from said inlet to said outlet.

6. The filter system of claim 5 wherein said first filter medium is selected from the group consisting of untreated carbon, activated carbon, activated charcoal and combinations thereof, and the second filter medium is selected from the group consisting of HEPA and non-woven filter media.

7. The filter system of claim 5 further including a water reservoir within said incubator, and a return filtered gas stream line connected between said outlet and said water reservoir so that the filtered gas stream passes through said water reservoir before returning to said gaseous environment.

8. The filter system of claim 5 further comprising a filter assembly unit, said filter and said pump being mounted in said filter unit and forming a self-contained structure.

9. The filter system of claim 8 wherein said filter unit is contained outside of said incubator.

10. The filter system of claim 8 wherein said filter unit is mounted within said incubator.

11. The filter system of claim 8 wherein said filter unit includes a housing having said inlet and outlet therein, a partition dividing said housing into two compartments, said pump being located in a first compartment and said filter being located in said second compartment, and further including an electrical power connector extending from said pump through said housing to a point external of said housing.

12. The filter system of claim 11 wherein said filter unit is located outside of said incubator, and further including an infeed gas line connected between the gaseous environment within the incubator and said inlet, and a moisture trap located in said infeed gas line and external of said incubator.

13. The filter system of claim 12 further including a connection device mounted in the wall of said incubator, said connection device including an inner face exposed to the interior of said incubator and an outer face exposed to the outside of said incubator, said connection device having a first and second bore extending therethrough, an outfeed port on said outer face communicating with said first bore, a line connecting said outfeed port with said moisture trap, a line connecting said moisture trap with said inlet on said filter unit, a gas stream inlet port on said outer surface of said connection device communicating with said second bore, a line connecting said outlet of said filter unit with said gas stream inlet port on said connector device.

14. The filter system of claim 13 further including a water reservoir within said cabinet, and wherein said connecting device has a gas port on its inner face communicating with said second bore, and further including a line connecting said gas port on said inner face with said water reservoir.

15. The filter system of claim 11 wherein said filter unit is contained within said incubator, and further including a connection device mounted in the wall of incubator, said connection device including an inner face exposed to the interior of said incubator and an outer face exposed to the outside of said incubator, said connection device having a bore therein extending between the inner and outer surfaces, said power cord extending from said filtering unit through said bore in said connecting device to a point external of said incubator.

16. A filter unit for use in filtering volatile organic contaminants and solid particulate material from the gaseous environment within an incubator comprising:
   a. a housing;
   b. a partition dividing said housing into first and second compartments;
   c. a pump located in said first compartment;
   d. a filter located in said second compartment;
   e. an electrical power connector extending from said pump through said housing to a point external of said housing;
   f. said housing having an inlet port to provide for the inflow of a gaseous stream from the interior environment of an incubator into the filter unit and an outlet port for providing of the outflow of filtered gas stream from the filter unit to the interior of the incubator; and
   g. said pump and said filter being connected between said inlet port and said outlet port so that said pump causes the flow of the gaseous stream into said inlet port through said pump and filter and through said outlet port to said incubator.

17. The filter unit of claim 16 wherein said housing includes a hinged door for providing access to said second compartment.

18. The filter unit of claim 16 wherein said filter includes a filter cartridge having an inlet and an outlet, and said pump has an intake port and an discharge port, and further including first and second spring biased quick connect/disconnect connectors in said partition each providing flow communication through said partition between said two compartments, said intake port of said pump being connected to the inlet port in said housing, said discharge port of said pump being connected to said first connector, said outlet port being connected to said second connector, and said filter cartridge having its inlet releasably connected to said first connector to permit flow through said connector into the filter cartridge and its outlet releasably connected to said second connector for flow from said filter through said second connection, said connectors preventing flow therethrough when said filter is disconnected.

19. The filter unit of claim 16 wherein said filter contains a first filter medium for filtering volatile organic compounds and a second filter medium for filtering solid particulate material.

20. The filter unit of claim 19 wherein said first filter medium is selected from the group consisting of untreated carbon, activated carbon, activated charcoal and combinations thereof, and the second filter medium is selected from the group consisting of HEPA and non-woven filter media.

21. A continuous process for filtering volatile organic compounds and particulate material from a gaseous environment in an incubator, said method comprising repeatedly performing the steps of:
   a. drawing a gas stream from the gaseous environment in the incubator;
   b. reducing the humidity in the drawn gas stream;
   c. passing the dehumidified gas stream through a filter assembly including a first filter medium which filters volatile organic compounds from said gas stream and a second filter medium which filters solid particulate material from said gas stream; and
   d. introducing the filtered gas stream back into the gaseous environment while continuing to draw off a gas stream from the incubator.

22. The process of claim 21 further comprising increasing the moisture content of the gas stream after it is filtered and before it is introduced back into the gaseous environment.

23. The process of claim 21 wherein said first filter medium is selected from the group consisting of un treated carbon, activated carbon, activated charcoal and combinations thereof, and said second filter medium is selected from the group consisting of HEPA and non-woven filter media.

24. The process of claim 21 wherein said gas stream has a flow rate of from about 0.1 to about 0.3 liters per minute.

25. A filter system for use with an incubator having a gas stream fed into the interior of the incubator from a gas source, said filter system comprising:
   a. a flow path for said gas stream, said flow path extending from said gas source to the interior of said incubator; and
   b. a filter assembly disposed between said gas source and the interior of said incubator for filtering said gas stream, said filter assembly including a first filter medium serving to filter volatile organic compounds from said gas stream and a second filter medium serving to filter solid particulate material from said gas stream.

26. The filter system of claim 25 wherein said first filter medium is selected from the group consisting of untreated carbon, activated carbon, activated charcoal and combinations thereof, and the second filter medium is selected from the group consisting of HEPA and non-woven filter media.

27. The filter system of claim 25, wherein said first filter medium is operable to substantially reduce amounts of styrene, n-decane and toluene organic compounds present in said gas stream entering said incubator.

28. The filter system of claim 27 wherein said first filter medium is operable to reduce amounts of styrene present in said gas stream entering said incubator to about 3.0 micrograms/meter$^3$.

29. The filter system of claim 27 wherein said first filter medium is operable to reduce amounts of n-decane present in said gas stream entering said incubator to about 14.0 micrograms/meter$^3$.

30. The filter system of claim 27 wherein said first filter medium is operable to reduce amounts of toluene present in said gas stream entering said incubator to about 4.8 micrograms/meter$^3$.

* * * * *